(12) United States Patent
Leybovich (10) Patent No.: US 6,895,342 B2
(45) Date of Patent: May 17, 2005

(54) METHOD AND APPARATUS FOR NON-DESTRUCTIVE TARGET CLEANLINESS CHARACTERIZATION BY TYPES OF FLAWS SORTED BY SIZE AND LOCATION

(75) Inventor: Alexander Leybovich, Hilliard, OH (US)

(73) Assignee: Tosoh SMD, Inc., Grove City, OH (US)

( * ) Notice: Subject to any disclaimer, the term of this patent is extended or adjusted under 35 U.S.C. 154(b) by 0 days.

(21) Appl. No.: 10/485,084
(22) PCT Filed: Jul. 23, 2002
(86) PCT No.: PCT/US02/23362
  § 371 (c)(1),
  (2), (4) Date: Jan. 26, 2004
(87) PCT Pub. No.: WO03/014718
  PCT Pub. Date: Feb. 20, 2003

(65) Prior Publication Data
  US 2004/0199337 A1 Oct. 7, 2004

Related U.S. Application Data
(60) Provisional application No. 60/311,152, filed on Aug. 9, 2001.

(51) Int. Cl.[7] ................................................. G01B 3/44
(52) U.S. Cl. ......................................................... 702/46
(58) Field of Search ............................ 702/46; 359/44; 73/599, 620, 601; 349/20, 161, 21; 313/509; 438/689; 148/432; 237/44; 420/469; 24/298

(56) References Cited

U.S. PATENT DOCUMENTS 2,790,216 A   4/1957   Hunter
4,054,173 A   10/1977  Hickam
4,568,007 A   2/1986   Fishler (Continued)

FOREIGN PATENT DOCUMENTS

EP   0 211 401 B1   5/1992
EP   0 418 846 B1   2/1995
EP   0 665 193 B1   8/1995
EP   0 467 659 B1   3/1996

(Continued)

OTHER PUBLICATIONS

Freitag, W.O. et al., "Diode Sputtering of Cermet Films," *2nd Symposium on Deposition of Thin Films by Sputtering*, University of Rochester and Consolidated Vacuum Corporation, Rochester, NY, Jun. 1967, pp. 92–96.

(Continued)

*Primary Examiner*—Bryan Bui
*Assistant Examiner*—Tung Lau
(74) *Attorney, Agent, or Firm*—Wegman, Hessler & Vanderburg (57) ABSTRACT

A preferred, non-destructive method for characterizing sputter target cleanliness includes the steps of sequentially irradiating the test sample with sonic energy predominantly of target sputter track areas; detecting echoes induced by the sonic energy; and discriminating texture-related backscattering noise from the echoes to obtain modified amplitude signals. These modified amplitude signals are compared with one or more calibration values so as to detect flaw data points at certain positions or locations where the comparison indicates the presence of at least one flaw. Most preferably, groups of the flaw data pixels corresponding to single large flaws are bound together so as to generate an adjusted set of flaw data points in which each group is replaced with a single, most significant data point. The adjusted set of flaw data point is used to calculate one or more cleanliness factors, or to plot a histogram, which characterizes the cleanliness of the sample.

15 Claims, 7 Drawing Sheets

U.S. PATENT DOCUMENTS

| | | | |
|---|---|---|---|
| 5,160,388 A | | 11/1992 | Legresy et al. |
| 5,369,063 A | | 11/1994 | Gee et al. |
| 5,406,850 A | | 4/1995 | Bouchard et al. |
| 5,559,614 A | * | 9/1996 | Urbish et al. ................ 349/21 |
| 5,636,681 A | | 6/1997 | Sulzer et al. |
| 5,738,767 A | | 4/1998 | Coad et al. |
| 5,827,409 A | | 10/1998 | Iwata et al. |
| 5,887,481 A | | 3/1999 | Leroy et al. |
| 5,943,559 A | | 8/1999 | Maeda |
| 5,955,673 A | | 9/1999 | Leroy et al. |
| 5,989,782 A | | 11/1999 | Nishiki et al. |
| 6,001,227 A | | 12/1999 | Pavate et al. |
| 6,017,779 A | | 1/2000 | Miyasaka |
| 6,019,657 A | | 2/2000 | Chakvorty et al. |
| 6,020,946 A | | 2/2000 | Callegari et al. |
| 6,057,557 A | | 5/2000 | Ichikawa |
| 6,139,701 A | | 10/2000 | Pavate et al. |
| 6,269,699 B1 | | 8/2001 | Gilman et al. |
| 6,487,910 B1 | | 12/2002 | Leybovich |

FOREIGN PATENT DOCUMENTS

| | | |
|---|---|---|
| EP | 0 412 843 B1 | 5/1996 |
| EP | 0 561 161 B1 | 4/1997 |
| WO | WO 97/30348 | 8/1997 |
| WO | WO 99/64854 | 12/1999 |
| WO | WO 00/15863 | 3/2000 |
| WO | WO 01/86282 | 11/2001 |
| WO | WO 02/081767 | 10/2002 |

OTHER PUBLICATIONS

Robinson, J.E. et al., "Models for Chunk Sputtering," *Journal of Nuclear Materials*, 1976, vol. 63, pp. 432–437, North–Holland Publishing Company.

Eernisse, E.P. et al., "Role of Integrated Lateral Stress in Surface Deformation of He–Implanted Surfaces," *Journal of Applied Physics*, Jan. 1, 1977, vol. 48, No. 1, pp. 9–17, American Institute of Physics.

Roth, R.M. et al., "Spatial Dependence of Particle Light Scattering in an RF Silane Discharge," *Appl. Phys. Letter*, Feb. 1, 1985, vol. 46, No. 3, pp. 253–255, American Institute of Physics.

Spears, K.G. et al., "Particle Distributions and Laser–Particle Interactions in an RF Discharge of Silane," *IEEE Transactions on Plasma Science*, Apr. 1986, vol. PS–14, No. 2, pp. 179–187, IEEE.

Anderson, H.M. et al., "Particulate Generation in Silane / Ammonia RF Discharges," *J. Applied Physics*, May 1, 1990, vol. 67, No. 9, pp. 3999–4011, American Institute of Physics.

Jellum, G.M. et al, "Particulates in Aluminum Sputtering Discharges," *J. Appl. Phys.*, May 15, 1990, vol. 67 No. 10, pp. 6490–6496, American Institute of Physics.

Selwyn, G.S. et al., "Particle Trapping Phenomena in Radio Frequency Plasmas," *Appl. Phys. Letter*, Oct. 29, 1990, vol. 57, No. 18 pp. 1876–1878, American Institute of Physics.

Akari, K. et al., "Reduction in Macroparticles During the Deposition of TiN Films Prepared by Arc Ion Plating," *Surface and Coatings Technology*, 1990, 43/44, pp. 312–323, Elsevier Sequoia, The Netherlands.

Barnes, M.S. et al., "Transport of Dust Particles in Glow–Discharge Plasmas," *Physical Review Letters*, Jan. 20, 1992, vol. 68, No. 3, pp. 313–316, The American Physical Society.

Smadi, M.M. et al., "Particle Contamination on a Silicon Substrate in a $SF_6$ / Ar Plasma," *J. Vac. Sci. Techol.*, Jan./Feb. 1992, B 10, (1) pp. 30–36, American Vacuum Society.

Logan, J.S. et al., "Study of Particle Emission in Vacuum from Film Deposits," *J. Vac. Sci. Technol.*, Jul./Aug. 1992, A 10, (4) pp. 1875–1878, American Vacuum Society.

Goree J. et al., "Particulate Release from Surfaces Exposed to a Plasma," *J. Vac. Sci. Techol.*, Nov./Dec. 1992, A 10, (6) pp. 3540–3544, American Vacuum Society.

Foster, H.I. et al., "A Modular Approach to Sputter Coating of Flat Panel Displays," *Society of Vacuum Coaters 35$^{th}$ Annual Technical Conference*, 1992, pp. 357–361.

Anderson, L., "A New Technique for Arc Control in DC Sputtering," *Society of Vacuum Coaters 35$^{th}$ Annual Technical Conference Proceedings*, 1992, pp. 325–329.

Nadel, S.J. et al., "Enhanced Chromium First Surface Mirrors," *Society of Vacuum Coaters, 35th Annual Technical Conference Proceedings*, 1992, pp. 365–369.

Scholl, R.A., "A New Method of Handling Arcs and Reducing Particulates in DC Plasma Processing," *Society of Vacuum Coaters 37th Annual Technical Conference Proceedings*, 1994, pp. 312–315, Advanced Energy Industries, Inc.

Lee, F. et al., "Detecting and Reducing Particles for LPCVD Silicon Nitride Deposition," *Microcontamination*, Mar. 1994, vol. 12, pp. 33–37, 76–77.

Bailey, R.S. et al., "Particle Emission from $Al_2O_3$ Doped Aluminum Targets During Sputtering Deposition," *VMIC Conference, ISMIC*, Jun. 7–8, 1994, p. 317.

Danovitch, D. et al., "Sputtering Issues for Flat–Panel Displays," *Information Display*, Nov. 1995, pp. 26–27, 30–31.

Selwyn, G.S. et al., "Particle Contamination Formation in Magneton Sputtering Processes," *J. Vac. Sci. Technol*, Jul./Aug. 1997, A 15 (4), pp. 2023–2028, American Vacuum Society.

Abburi, M. et al., "Low–Defect Target Metallurgy Development for sub–0.18 µm Al–based Interconnects," *Solid State Technology*, Dec. 1999, vol. 42, pp. 55–58, Solid State Technology.

\* cited by examiner

METHOD AND APPARATUS FOR NON-DESTRUCTIVE TARGET CLEANLINESS CHARACTERIZATION BY TYPES OF FLAWS SORTED BY SIZE AND LOCATION

CROSS-REFERENCE TO RELATED APPLICATIONS

Priority filing benefit of (1) International PCT application PCT/US02/23362 filed Jul. 23, 2002, and published under PCT 21(2) in the English language and (2) U.S. Provisional Application Ser. No. 60/311,152 filed Aug. 9, 2001.

FIELD OF THE INVENTION

This invention relates to non-destructive methods and apparati for detection of types of minute flaws which may be present in sputter targets and, more particularly, to non-destructive methods and apparati for target volumetric cleanliness characterization by types of flaws sorted by size and location.

BACKGROUND OF THE INVENTION

Cathodic sputtering is widely used for depositing thin layers or films of materials from sputter targets onto desired substrates such as semiconductor wafers. Basically, a cathode assembly including a sputter target is placed together with an anode in a chamber filled with an inert gas, preferably argon. The desired substrate is positioned in the chamber near the anode with a receiving surface oriented normally to a path between the cathode assembly and the anode. A high voltage electric field is applied across the cathode assembly and the anode.

Electrons ejected from the cathode assembly ionize the inert gas. The electrical field then propels positively charged ions of the inert gas against a sputtering surface of the sputter target. Material dislodged from the sputter target by the ion bombardment traverses the chamber and deposits on the receiving surface of the substrate to form the thin layer or film.

One factor affecting the quality of the layer or film produced by a sputtering process is the "cleanliness" of the material from which the sputter target is made. Since the cleanliness of the material from which a sputter target is made affects the quality of layers or films produced using that target, it is obviously desirable to use relatively clean materials in fabricating sputter targets.

However, since the target material consumption during the sputtering process is highly non-uniform (this is especially true for modern sputter-deposition tools with planar magnetron sources using a specifically-confined non-uniform magnetic fields formed by rotating or stationary magnets), localized highly eroded regions or "sputter tracks" typically form on the surface of the target. Although the sputter track region of the target is heavily eroded, other regions of the target experience significantly less erosion or even remain practically unsputtered. Due to this difference in erosion intensity, there is a substantial difference in the contribution of different target regions to the sputtering process. While the material cleanliness of the heavily-eroded sputter track region is absolutely critical for the film quality, the cleanliness of the regions where insignificant sputtering or no sputtering occurs is less critical.

As presently understood, prior art cleanliness criteria did not distinguish the "sputter track" and "non-sputter track" regions of the target surface. Thus, prior art techniques for characterizing sputter targets did not take into account the possibility that, in a field where a few or even one single minute flaw can impact on a decision to accept or reject a target, identifying flaw size and determining whether flaws are located inside or outside the sputter track regions can improve target production yield without compromising the functional target quality.

Figure 1:
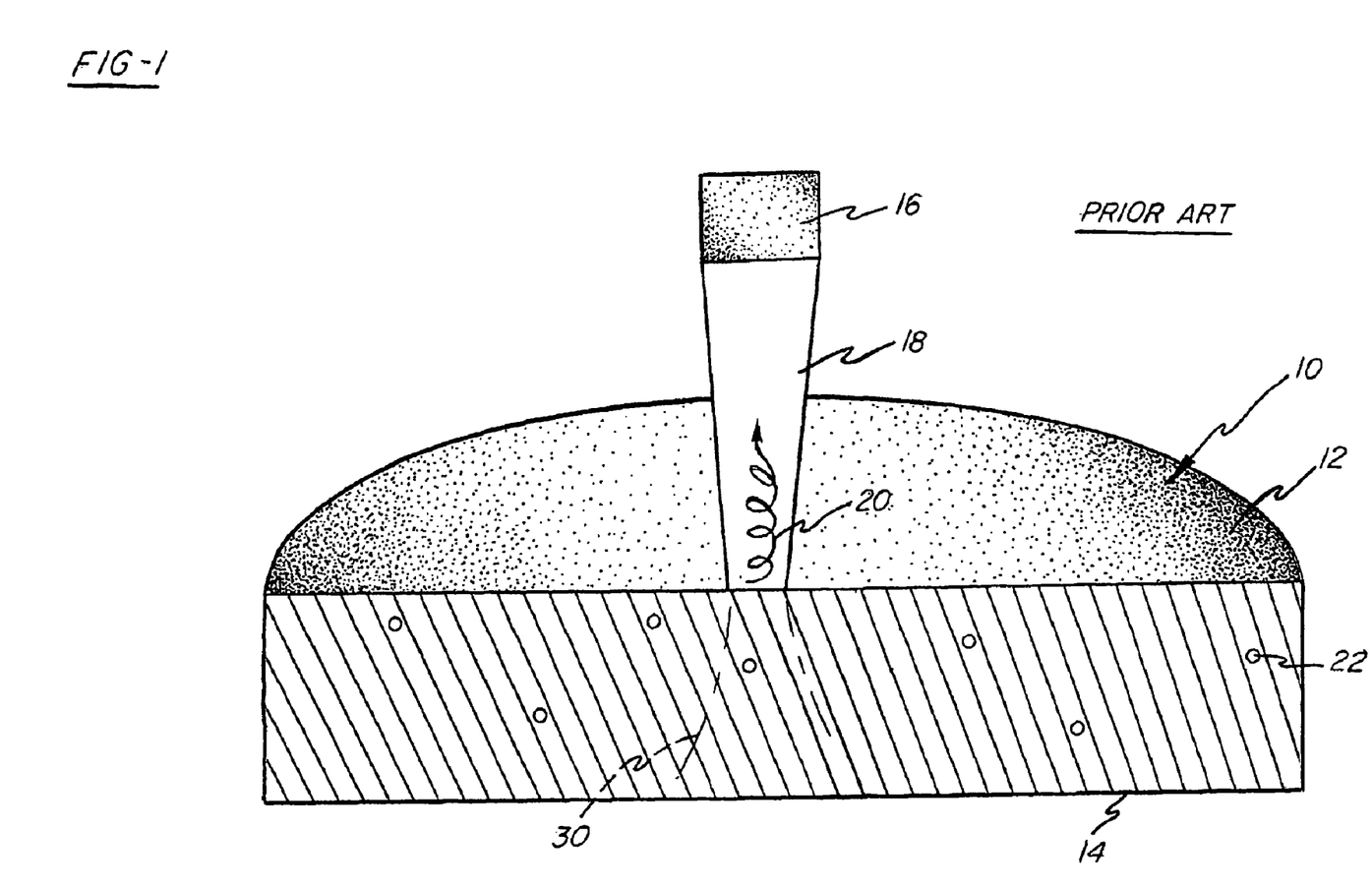
FIG. 1 is a schematic view illustrating a first prior art method of ultrasonic texture analysis.

For example, FIG. 1 illustrates a technique for characterizing aluminum and aluminum alloy sputter targets similar to the methods proposed in Leroy et al. U.S. Pat. Nos. 5,887,481 and 5,955,673. The technique illustrated in FIG. 1 employs a pulse-echo method performed on a test sample 10 having a planar upper surface 12 and a parallel planar lower surface 14. In accordance with this technique, focused ultrasonic transducer 16 irradiates each of a sequence of positions on the upper surface 12 of the test sample 10 with a single, short-duration, high-frequency ultrasound pulse 18 having a frequency of at least 5 MHz, and preferably 10–50 MHz. The ultrasonic transducer 16 then switches to a sensing mode and detects a series of echoes 20 induced by the ultrasound pulse 18.

One factor which contributes to these echoes 20 is scattering of sonic energy from the ultrasound pulse 18 by flaws 22 in the test sample 10. By comparing the amplitudes of echoes 20 induced in the test sample 10 with the amplitudes of echoes induced in reference samples (not shown) having compositions similar to that of the test sample 10 and blind, flat-bottomed holes of fixed depth and diameter, it is possible to detect and count flaws 22 in the test sample 10.

The number of flaws detected by the technique of FIG. 1 has to be normalized in order to facilitate comparison between test samples of different size and geometry. Conventionally, the number of flaws is normalized by volume, that is, the sputter target materials are characterized in units of "flaws per cubic centimeter." The volume associated with the echoes 20 from each irradiation of the test sample 10 is determined, in part, by estimating an effective cross-section of the pulse 18 in the test sample 10.

A number of factors detract from the ability of the transducer 16 to detect sonic energy scattered by the flaws 22. This reduces the sensitivity of the technique.

One such factor is relative weakness of the scattered energy. A portion of the scattered energy is attenuated by the material making up the test sample 10. Furthermore, since the flaw sizes of interest, which range from approximately 0.04 mm to 1 mm, are of same order or less than the wavelength of ultrasound in metals (for example, the wavelength of sound in aluminum for the frequency range of 10 MHz is 0.6 mm), the pulse 18 has a tendency to refract around the flaws 22, which reduces the scattering intensity.

Another factor detracting from the ability of the transducer 16 to detect the sonic energy scattered by the flaws 22 is the noise generated by scattering of the pulse 18 at the boundaries between grains having different textures. In fact, the texture-related noise can be so great for high-purity aluminum having grain sizes on the order of several millimeters that small flaws within a size range of approximately 0.05 mm to 0.4 mm and less cannot be detected. Larger grain sizes reduce the signal-to-noise ratio for the sonic energy scattered by the flaws when compared to the noise induced by the grain boundaries.

Other factors affecting the sensitivity and resolution of the technique of FIG. 1 includes the pulse frequency, duration and waveform; the degree of beam focus and the focal spot size; the coupling conditions, that is, the efficiency with which the sonic energy travels from the transducer 16 to the test sample 10; and the data acquisition system parameters.

Another drawback to the technique of FIG. 1 is that the calculation of the "flaws per cubic centimeter" in the test sample 10 presupposes that only flaws 22 within a determinable cross-sectional area scatter sonic energy back toward the transducer 16. In fact, the pulse 18, due to its wave nature, does not have localized, well-determined boundaries.

The distribution of the energy of the pulse 18 within the test sample 10, under simplifying assumptions, permits one to define a corridor 30 having a determinable cross-section beneath the transducer 16 in which most of the energy should be concentrated. Nevertheless, some of the energy of the pulse 18 will propagate outside this corridor 30. As a result, the transducer may detect sonic energy scattered by relatively large flaws 22 located outside the estimated corridor 30, thereby overestimating the density of flaws 22 in the test sample 10 and underestimating their sizes. Because of this, material cleanliness characteristics become to some degree uncertain.

Another drawback to the technique of FIG. 1 is inability to determine the proximity of a flaw to the sputter track region. This increases the risk that a manufacturer will accept targets which are undesirable because of defects located at or near the sputter track regions. Alternatively, it increases the risk that the manufacturer will reject potentially useful targets to compensate for the risk of accepting targets having unacceptable defects in or near the sputter track region.

Thus, there remains a need in the art for non-destructive techniques for characterizing sputter target materials having greater sensitivity than the method illustrated in FIG. 1. There also remains a need for techniques which permit the comparison of the cleanliness of different sputter target materials in a manner which is not dependent on arbitrary volumetric estimations in the form of "flaws per cubic unit."

Partially, these drawbacks and limitations have been overcome by the prior art technique suggested in Tosoh SMD International Application No. PCT/US99/13066. Application PCT/US99/13066 discloses a method which overcomes most, though not necessarily all, of the disadvantages stated above. Since the data collection, analysis and imaging techniques proposed in Application PCT/US99/13066 are intended to detect, identify, and count flaws with sizes in the range of 0.04 mm to 0.1 mm (that is, flaws having relative sizes less than the size of the single pixel of the data acquisition and displaying device), each single flaw is represented by the single data point (pixel) with a value equal to the signal amplitude.

Figure 2:
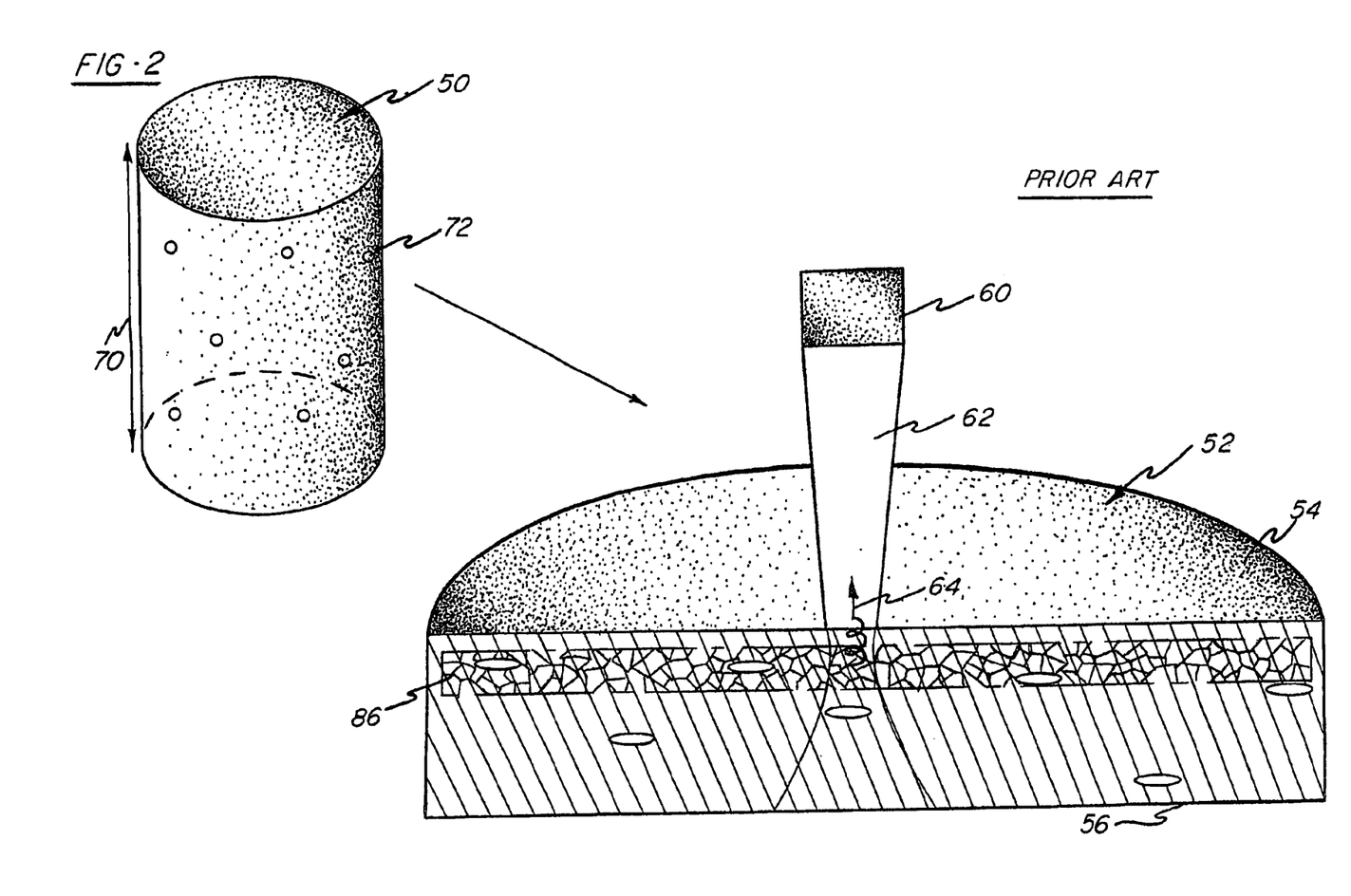
FIG. 2 is a schematic view illustrating a second prior art method of ultrasonic texture analysis.

The technique according to Application No. PCT/US99/13066 counts the total number of flaw data points or pixels "$C_F$," to quantify the degree of target material cleanliness. FIG. 2 illustrates this method for characterizing the cleanliness of sputter target material. In accordance with this method, a cylindrical sample 50 of the sputter target material is compressed or worked to produce a disc-shaped test sample 52 having a planar upper surface 54 and a substantially parallel planar lower surface 56. Thereafter, a focused ultrasonic transducer 60 is positioned near the upper surface 54. The transducer 60 irradiates the upper surface 54 of the test sample 52 with a single, short-duration, megahertz-frequency-range ultrasonic pulse 62. The transducer 60 subsequently detects an echo 64 induced in the test sample 52 by the pulse 62. The transducer 60 converts the echo 64 into an electrical signal (not shown), which is processed for use in characterizing the test sample 52.

Figure 3:
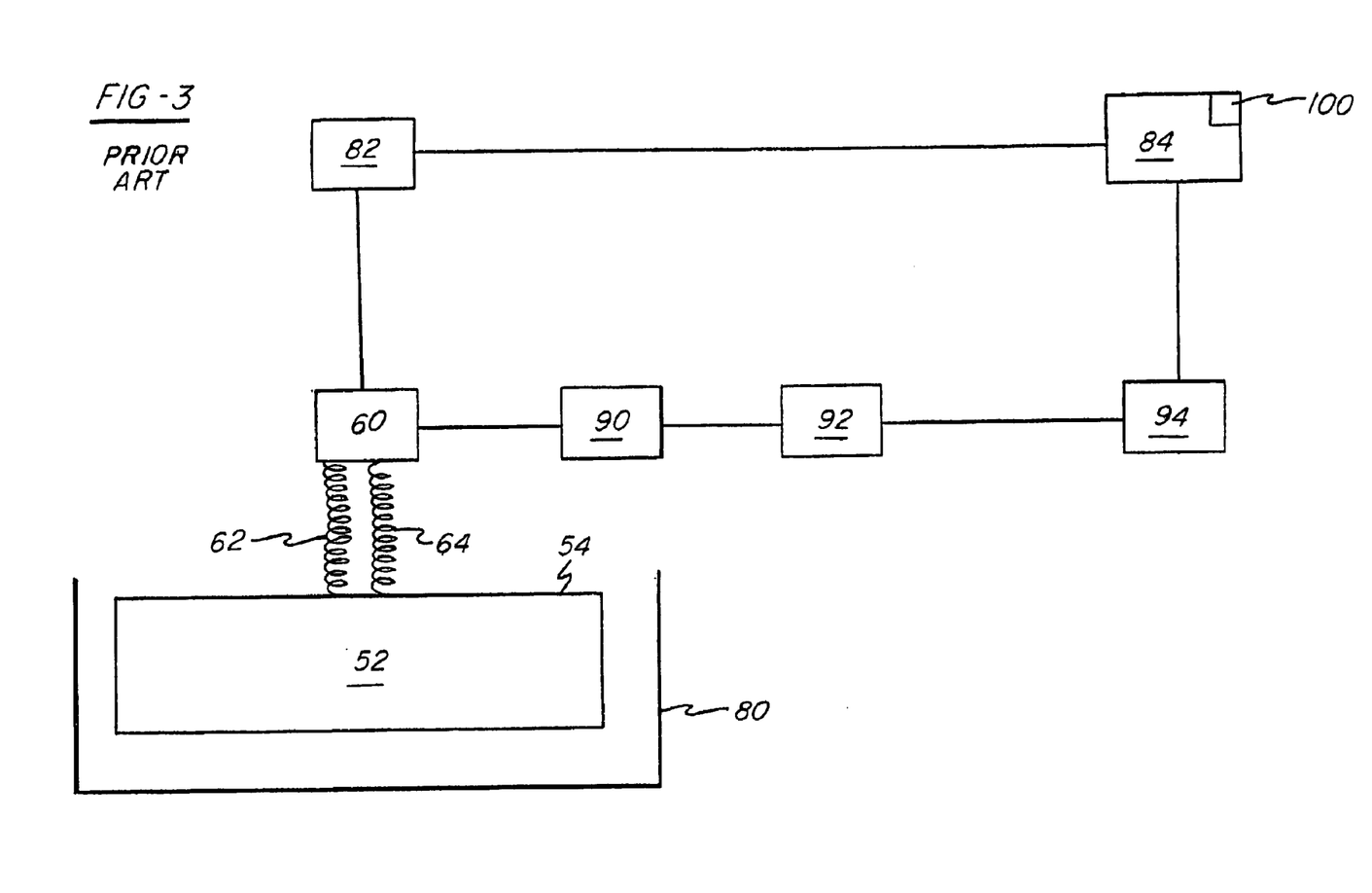
FIG. 3 is a schematic view of an apparatus for carrying out the method of FIG. 2.

As illustrated in FIG. 3, the test sample 52 first is immersed in deionized water (not shown) in a conventional immersion tank 80. The transducer 60 is mounted on a mechanical X-Y scanner 82 in electrical communication with a controller 84, such as a PC controller. The controller 84 is programmed in a conventional manner to induce the mechanical X-Y scanning unit 82 to move the transducer 60 in a raster-like stepwise motion across the upper surface 54 of the test sample 52.

The transducer 60 is oriented so that the pulse 62 propagates through the deionized water (not shown) in the immersion tank 80 and strikes the test sample 52 approximately normally to the upper surface 54. The transducer 60 preferably is spaced from the upper surface 54 such that the pulse 62 is focused on a zone 86 (FIG. 2) of the test sample 52.

An echo acquisition system for use in the method of FIGS. 2 and 3 includes a low noise gated preamplifier 90 and a low noise linear amplifier 92 with a set of calibrated attenuators. When sufficient time has elapsed for the echoes to arrive at the transducer 60, the controller 84 switches the transducer 60 from a transmitting mode to a gated electronic receiving mode. The echoes 64 are received by the transducer 60 and converted into an RF electric amplitude signal (not shown). The amplitude signal is amplified by the preamplifier 90 and by the low noise linear amplifier 92 to produce a modified amplitude signal. The attenuators (not shown) associated with the low noise linear amplifier 92 attenuate a portion of the texture-related noise. The modified amplitude signal then is digitized by the analog-to-digital converter 94 before moving on to the controller 84. The analog-to-digital conversion is performed so as to preserve amplitude information from the analog modified amplitude signal.

Flaws of given sizes are detected by comparing the digitized modified amplitude signals obtained from the sample 52 with reference values derived from tests conducted on reference samples (not shown) having compositions similar to that of the test sample 52 and blind, flat-bottomed holes of fixed depth and diameter.

The PC controller 84 includes a microprocessor 100 programmed to control the data acquisition process. The microprocessor 100 also is programmed to calculate the cleanliness factor characterizing the material of the samples 50, 52. It discriminates the texture-related backscattering noise and distinguishes "flaw data points," that is, data points where comparison of the digitized, modified amplitude signals with the reference values indicate the presence of flaws. The microprocessor 100 maintains a count of the flaw data points detected during the testing of a test sample 52 to determine the "flaw count" $C_F$. The microprocessor 100 also is programmed to distinguish "no-flaw data points," that is, data points where comparison of the digitized, modified amplitude signals with the calibration values indicates the absence of flaws.

The microprocessor 100 also determines a total number of data points "$C_{DP}$," that is, the sum of the flaw count $C_F$ and the number of no-flaw data points. Although the total number of data points could be determined by adding the counts of the flaw data points and the no-flaw data points, it preferably is determined by counting the total number of positions "$C_1$" along the upper surface 54 at which the test sample 52 is irradiated by the transducer 60 and subtracting the number of digitized RF signals "$C_N$" which the data acquisition circuitry was unable, due to noise or other causes, to identify as either flaw data points or no-flaw data points. Having determined the flaw count $C_F$ and the total number of data points $C_{DP}$, the microprocessor is programmed to calculate a cleanliness factor $F_C=(C_F/C_{DP})\times 10^6$ to characterize the material comprising the samples 50, 52.

Another way in which the method of FIG. 2 characterizes the material comprising the samples 50, 52 is by determining the size distribution of flaws in the test sample 52. More specifically, the method characterizes the cleanliness of the sample 52 by defining amplitude bands or ranges; comparing the amplitudes of the digitized, modified amplitude signals with the amplitude bands so as to form subsets of the modified amplitude signals; counting the data points in these subsets of modified amplitude signals to determine a modified amplitude signal count for each amplitude band; and constructing a histogram relating the modified signal counts to said plurality of amplitude bands. Since the amplitudes represented by the digitized, modified amplitude signals are related to the sizes of flaws detected in the sample 52, the histogram provides an indication of the flaw size distribution in the sample 52.

However, it has to be taken into consideration that a single flaw with size larger than about 0.1 mm may not be represented by one single data point. For example, a single flaw larger than about 0.1 mm may exceed the effective cross-section of a single pulse. This possibility makes it more difficult or even impossible to determine the total number of flaws based on the raw count of flaw data points or pixels.

Another drawback to the methods of FIGS. 1–3 is that they are designed to test and characterize one target or sample (not shown) at a time. That is, the methods as proposed in the references appear to have been designed to conduct each test sequentially and without overlap even when a queue of targets or samples (not shown) becomes available for testing in the course of a manufacturing process.

Thus, there remains a need in the art for non-destructive techniques to characterize cleanliness of sputtering target which are able to identify and properly count the flaws with greater range of flaw sizes and to provide separate flaw counts for sputter track and non-sputter track regions.

SUMMARY OF THE INVENTION

These needs and others are addressed by means of a non-destructive method for characterizing a test sample of a sputter target material defining a sputtering surface. A preferred method includes the steps of sequentially irradiating the test sample with sonic energy at a plurality of positions on the surface; detecting echoes induced by the sonic energy; and discriminating texture-related backscattering noise from the echoes to obtain modified amplitude signals. These modified amplitude signals are compared with one or more calibration values so as to detect flaw data pixels or points at certain positions or locations where the comparison indicates the presence of at least one flaw as well as no-flaw data pixels at other positions where the comparison indicates an absence of flaws. Most preferably, groups of the flaw data pixels corresponding to single large flaws are bound together so as to generate an adjusted set of flaw data points in which each group of the groups of flaw data pixels is replaced with a single, most significant data point.

In accordance with one especially preferred embodiment, members of the adjusted set of flaw data points are counted to determine at least one flaw count $C_F$. A total number of data points $C_{DP}$ is determined and a cleanliness factor $F_C=(C_F/C_{DP})\times 10^6$ is calculated. This cleanliness factor serves to characterize the cleanliness of the sputter target material.

In accordance with another especially preferred embodiment, a plurality of amplitude bands are defined. The amplitudes represented by members of the adjusted set of flaw data points are compared with the amplitude bands to form a plurality of subsets of the adjusted set of flaw data points, where "n" is the number of the subsets of the adjusted set of flaw data points. Then, members of the subsets of the adjusted set of flaw data points are counted to determine a plurality of flaw counts $C_{F1}, \ldots C_{Fn}$. The plurality of flaw counts is used to construct a histogram relating the flaw counts $C_{F1}, \ldots C_{Fn}$ to said amplitude bands. This histogram then serves to characterize the cleanliness of the sputter target material.

In accordance with yet another especially preferred embodiment, the flaw data points are classified according to size or location on the upper surface of the test sample. In accordance with one such method, each data point is associated with a position on the surface of the test sample. Only flaw data points associated of the plurality of positions located proximate the sputter track region are included in the adjusted set of flaw data points which is counted to determine the flaw count and the cleanliness factor.

In accordance with another such method, the members of the adjusted set of flaw data points is classified according to ranges of size to form a plurality of subsets of size-classified flaw data points, where "n" represents the number of sets in the plurality of subsets of size-classified flaw data points. The members of each of the plurality of subsets of size classified flaw data points are counted to determine flaw counts $C_{F1}, \ldots C_{Fn}$. Then, a plurality of cleanliness factors $F_{Cj}=(C_{Fj}/C_{DP})\times 10^6$ are calculated to characterize the sputter target material.

Preferred apparatus for non-destructive characterization of a test sample of a sputter target material comprises an ultrasonic transducer for irradiating the test sample with sonic energy and detecting echoes induced by the sonic energy to generate RF electric amplitude signals; an X-Y scanner mounting the ultrasonic transducer for controlled movement of the ultrasonic transducer relative to the surface of the test sample; a pre-amplifier for receiving and amplifying the RF electric amplitude signals; a linear amplifier with a set of calibrated attenuators for generating modified amplitude signals related to the RF electric amplitude signals; an analog-to-digital converter for receiving the modified amplitude signals and generating digital signals related to said modified amplitude signals; and a microprocessor controller. Most preferably, the microprocessor controller includes a first microprocessor and a second microprocessor. In accordance with an especially preferred apparatus, the first microprocessor is programmed to regulate the controlled movement of the ultrasonic transducer relative to the surface; to receive the digital signals, and to transfer the digital signals to the second microprocessor. The second microprocessor is programmed to compare the modified amplitude signals with the one or more calibration values to detect flaw data points at certain where comparison of the modified amplitude signals with the one or more calibration values indicates at least one flaw; and to detect no-flaw data points at other positions where comparison of the modified amplitude signals with the at least one calibration value indicates no flaw. In addition, the second microprocessor is programmed to bind groups of the flaw data points corresponding to single large flaws so as to generate an adjusted set of flaw data points in which each group of the groups of flaw data points is replaced with a single, most significant data point; to count members of the adjusted set of flaw data points to determine at least one flaw count $C_F$; to determine a total number of data points $C_{DP}$; and to calculate a cleanliness factor $F_C=(C_F/C_{DP})\times 10^6$.

Unlike the prior art method described earlier, the method of the present invention provides a characterization of the target cleanliness for different sputtering-affected regions of the target separately, that makes it possible to establish different cleanliness specification for different sputter regions and to improve the target production yield.

Furthermore, unlike the prior art method, the method of the present invention provides a characterization of the cleanliness of sputter target material for sputter track region separately by counting the flaw at least for three size ranges such as the size range which is less or equal to 0.5 mm, the size range which is of 0.5 mm to 0.8 mm, and the size range which is equal to or larger 0.8 mm.

Most preferably, the test sample is compressed along one dimension, such as by rolling or forging, and then irradiated by sonic energy propagating transversely, that is, obliquely or, better yet, normally, to that dimension. This has the effect of flattening and widening any flaws in the material. The widening of the flaws, in turn, increases the intensity of the sonic energy scattered by the flaws and reduces the likelihood that the sonic energy will refract around the flaws.

These methods for characterizing sputter target materials may be used in processes for manufacturing sputter targets. As noted earlier, the cleanliness of a sputter target is one factor determining the quality of the layers or films produced by the target. By processing only those sputter target blanks having cleanliness characteristics meeting certain reference criteria for sputter track and non-sputter track regions and rejecting blanks not meeting those criteria, one improves the likelihood that the sputter targets so manufactured will produce high quality layers or films at the same time the manufacturer's production yield can be increased reducing the cost of production and increasing production throughput.

Therefore, it is one object of the invention to provide an improved non-destructive methods for characterizing sputter target materials. Other objects of the invention will be apparent from the following description, the accompanying drawings, and the appended claims.

DETAILED DESCRIPTION OF THE PREFERRED EMBODIMENT

Figure 4:
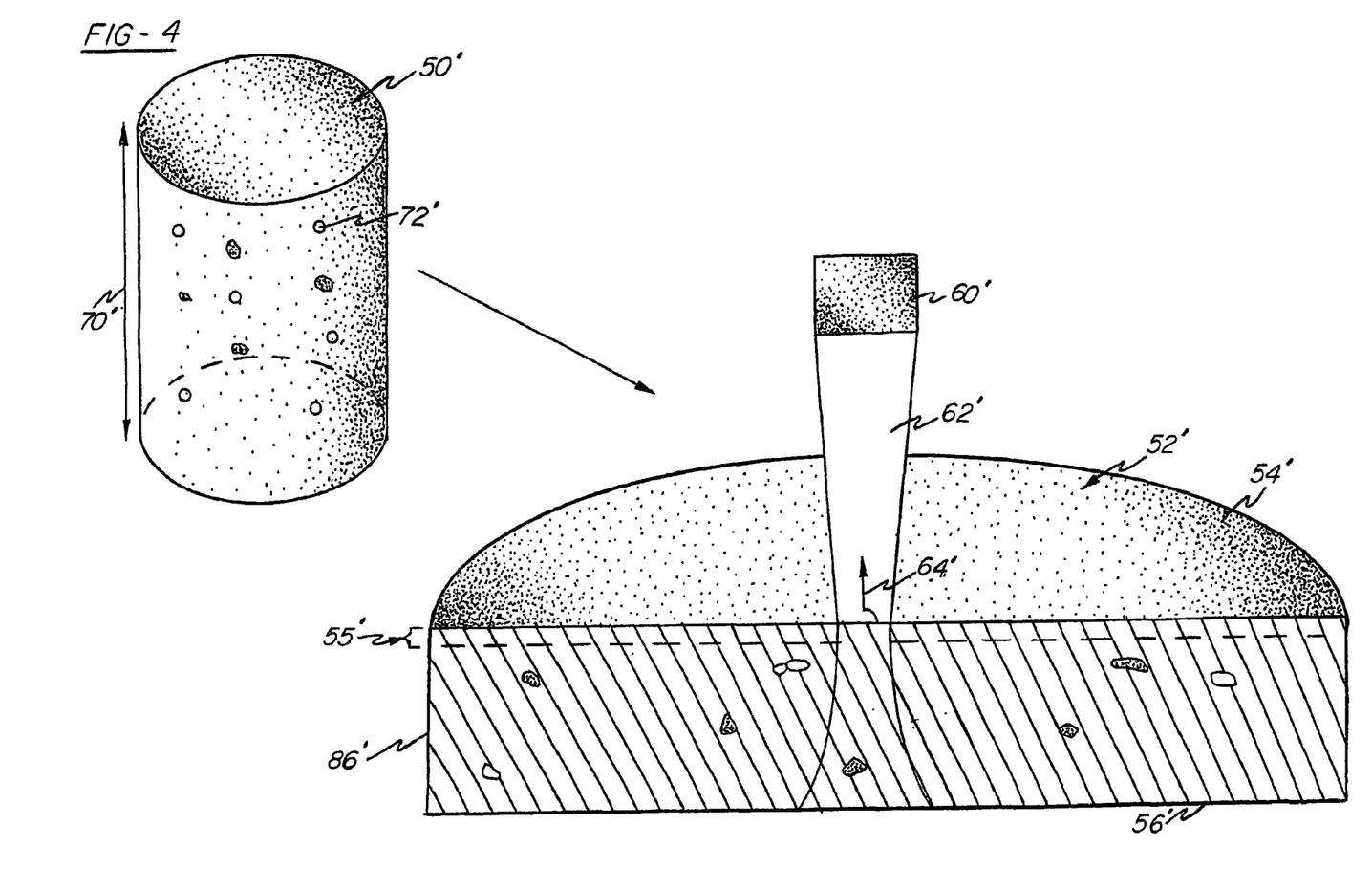
FIG. 4 is a schematic view illustrating an especially-preferred method of ultrasonic cleanliness characterization in accordance with the invention.

FIG. 4 illustrates an especially-preferred method for characterizing the cleanliness of sputter target material. In accordance with this method, a cylindrical sample 50' of the sputter target material (which preferably comprises metal or a metal alloy) is compressed or worked to produce a disc-shaped test sample 52' having a planar upper surface 54' and a substantially planar lower surface 56' approximately parallel to the upper surface 54'. Thereafter, a focused ultrasonic transducer 60' is positioned near the upper surface 54'. The transducer 60' irradiates the entire upper surface 54' of the test sample 52', or a region of the upper surface 54' less than the entire surface, with single, short-duration, megahertz-frequency-range ultrasonic pulses 62'. The transducer 60' subsequently detects echoes 64' induced in the test sample 52' by the pulses 62'. The transducer 60' converts the echoes 64' into electrical signals (not shown), which are processed for use in characterizing the test sample 52'.

More specifically, the sample 50' first is compressed along a dimension 70' to form the disc-shaped test sample 52'. Preferably, the sample 50' is compressed by forging or rolling of the sample 50', followed by diamond cutting to prepare the planar surfaces 54' and 56'. The compression of the sample 50' flattens and widens any flaws 72', so as to increase the surface area of the flaws 72' normal to the dimension 70'.

Figure 5:
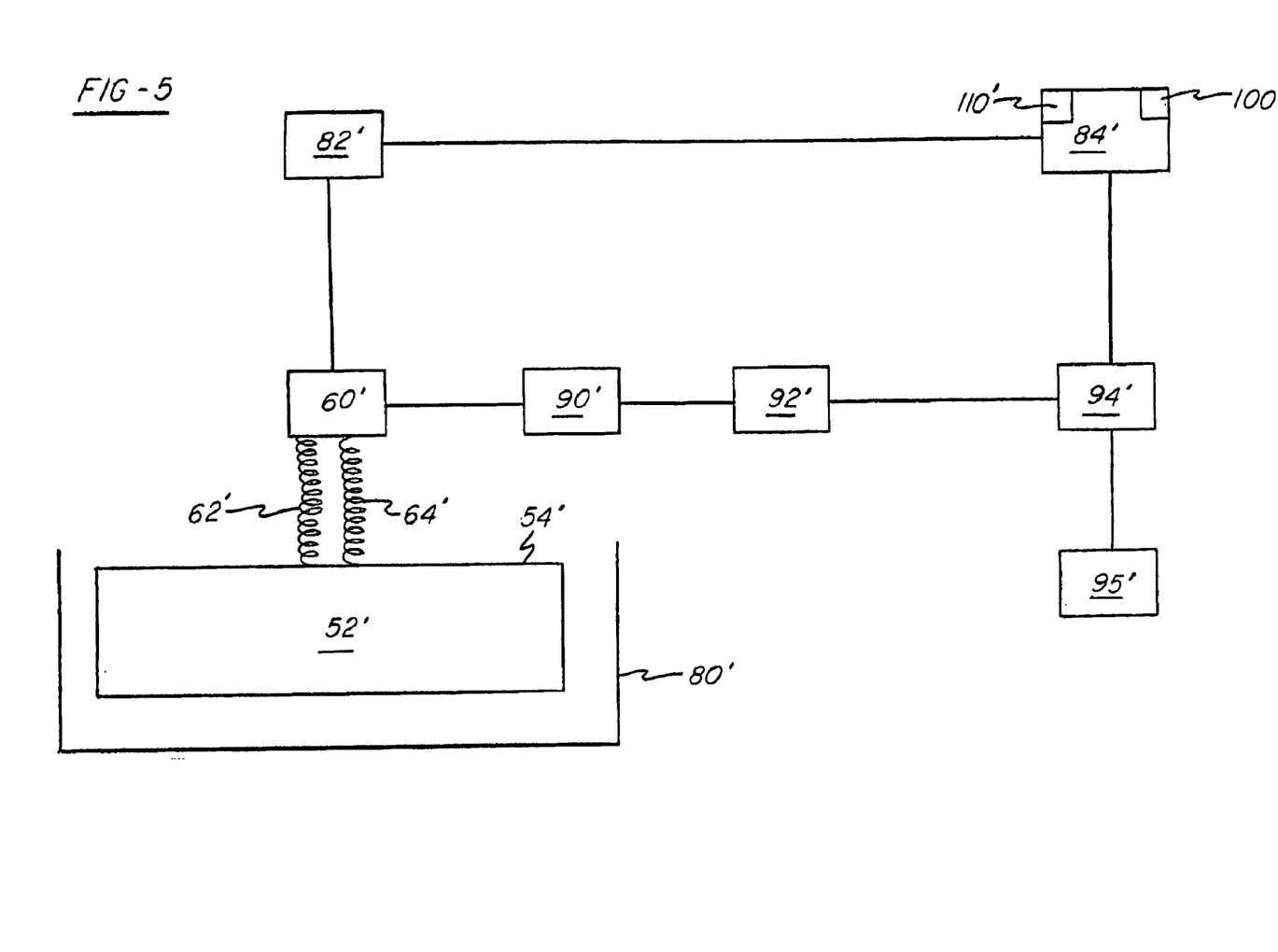
FIG. 5 is a schematic view of an apparatus for carrying out the method of FIG. 4.

As illustrated in FIG. 5, the test sample 52' then is immersed in deionized water (not shown) in a conventional immersion tank 80'. The transducer 60' is mounted on a mechanical X-Y scanner 82' in electrical communication with a controller 84' such as a PC controller. The controller 84' is programmed in a conventional manner to induce the mechanical X-Y scanning unit 82' to move the transducer 60' in a raster-like stepwise motion across the upper surface 54' of the test sample 52'.

The presently preferred transducer 60' is sold by ULTRAN USA under the designation WS50-10-P4.5. This is a high resolution piezoelectric transducer having a fixed focalization distance. At a peak frequency of approximately 10 MHz with an 8 MHz (−6 dB) bandwidth, the transducer produces a pulse 62' having a focal distance of approximately 115 mm and a focal spot of approximately 0.6 mm in diameter.

Most preferably, the upper surface 54' of the sample 52' has a width or diameter on the order of approximately 13 inches (approximately 33 cm). Data acquisition steps of approximately 0.8 mm in both the X-direction and the Y-direction permit the detection of flaws equivalent to a 0.25 mm blind flat-bottom hole located at the back wall of a 25 mm thick reference standard at a detection level of −6 dB without exposure area overlap. One thereby irradiates approximately 140,000 test points on the upper surface 54'.

It is within the contemplation of the invention to irradiate only a region of the upper surface 54' of the sample 52', such as the sputter track region (not shown). More specifically, it is within the contemplation of the invention to program the microprocessor controller 84' so as to induce the X-Y scanning unit 82' to scan only points in or near a region of interest (not shown) less than the entire upper surface 54'. The preparation of a suitable program for accomplishing this is within the ordinary skill in the art and requires no undue experimentation.

Most preferably, the transducer 60' is oriented so that the pulse 62' propagates through the deionized water (not shown) in the immersion tank 80' and strikes the test sample 52' approximately normally to the upper surface 54'. Furthermore, the transducer 60' is preferably spaced from the upper surface 54' such that the pulse 62' is focused on a zone 86' (FIG. 4) of the test sample 52'. The preferred zone 86' is approximately 25 mm thick and is separated from the upper surface 54' by an interval 55' of approximately 4.5 mm. The pulse 62' interacts with the sample 52' to induce echoes 64', which then propagate back through the deionized water (not shown) to the transducer 60' approximately 60 μsec after the pulse is sent.

An especially-preferred echo acquisition system includes a low noise gated preamplifier 90'; a low noise linear amplifier 92' with a set of calibrated attenuators (not shown) having a signal-to-noise (texture) ratio which identifies definitely a signal equivalent to that from a blind, flat-bottom hole of 0.25 mm in diameter located 25 mm below upper surface 54'; a 12-bit (2.44 mV/bit) analog-to-digital converter 94'; and, optionally, a digital oscilloscope 95'. When sufficient time has elapsed for the echoes to arrive at the transducer 60', the controller 84' switches the transducer 60' from a transmitting mode to a gated electronic receiving mode. The echoes 64' are received by the transducer 60' and converted into an RF electric amplitude signal (not shown). The amplitude signal is amplified by the preamplifier 90' and then filtered by the low noise linear amplifier 92' to produce a modified amplitude signal. The modified amplitude signal then is digitized by the analog-to-digital converter 94' before moving on to the controller 84'. The analog-to-digital conversion is performed so as to preserve amplitude information from the analog modified amplitude signal.

The especially-preferred PC controller 84' includes a first microprocessor 100' and a second microprocessor 110'. The first microprocessor 100' is programmed to control the movement of the transducer 60' and the data acquisition process. An especially-preferred software package used in connection with the data acquisition system is available from Structural Diagnostics, Inc. under the designation SDI-5311 Winscan 4.

To improve the overall productivity of the system, the acquired raw data information is transferred in the form of a raw data file (not shown) to the second microprocessor 110'. The division of data acquisition and data processing tasks between the first and second microprocessors 100', 110' facilitates the performance of uninterrupted, continuous and simultaneous data acquisition and data processing for a group of samples (not shown), allowing two of the samples (not shown) to be processed simultaneously. While the sample 52' is subjected to the data acquisition process controlled by the first microprocessor 100', another sample (not shown) with previously acquired data is analyzed for cleanliness by the second microprocessor 110'. This division of labor improves the overall test productivity when a queue of samples (not shown) can be expected.

The preferred samples 52' take the form of flat discs which are inscribed into the X-Y raster-type scanning envelope. As a consequence, the second microprocessor 110' extracts only target-related data points from the raw data. That is, the second microprocessor 110' is programmed to "crop" the data so that only data points taken from locations internal to the surface 54' are processed and boundary data points are excluded.

The second microprocessor 110' also is programmed to calculate one or more cleanliness factors characterizing the material of the samples 50' (FIG. 4), 52'. More precisely, it is programmed to discriminate texture-related backscattering noise so as to distinguish flaw-related data points, that is, data points where comparison of the digitized, modified amplitude signals with the reference values indicates the presence of flaws. It maintains a count of the flaw data points detected during the testing of a test sample 52', either throughout the entire upper surface 54' (FIG. 4) or within a particular region of interest such as the sputter track region (not shown), to determine one or more "flaw counts" $C_F$. The second microprocessor 110' also is programmed to distinguish "no-flaw data points," that is, data points or pixels where comparison of the digitized, modified amplitude signals with the calibration values indicates the absence of flaws.

The second microprocessor 110' also is programmed to calculate the total number of flaws per the sample falling into three distinct size ranges with flaw sizes equal to, or smaller than, 0.5 mm; with flaw sizes in the range of 0.5 mm to 0.8 mm; and with flaw sizes equal to, or larger than, 0.8 mm.

The second microprocessor 110' also is programmed to analyze the plurality of data points (pixels) in respect to their physical location outside or inside of the sputter track region (not shown) or another region of interest (not shown). One means for accomplishing this is to associate each digitized, modified amplitude signal with the location (not shown) of the transducer 60' in the X-Y raster grid (e.g., by means of the order in which the data points are arranged in the raw data file (not shown) transferred from the first microprocessor 100') where the echo 64' which produced that digitized, modified amplitude signal was induced; and to compare that location (not shown) with the position of the sputter track region (not shown) or other region of interest (not shown) on the upper surface 54' of the sample 52'. In accordance with a particularly preferred method, the second microprocessor 110' is programmed to determine the number of flaws located inside the sputter track region (not shown) which fall into the three distinct size ranges, namely, with flaw sizes equal to, or smaller than, 0.5 mm; with flaw sizes in the range of 0.5 mm to 0.8 mm; and with flaw sizes equal to, or larger than, 0.8 mm.

The second microprocessor 110' also is programmed to analyze a plurality of data points or pixels (not shown) in the way which binds groups of data points representing a single flaw (not shown) of a size larger than that represented by a single data point or pixel. In other words, when the second microprocessor 110' detects a flaw data point having a digitized, modified amplitude value greater than a threshold value, it is programmed to examine the data points associated with locations on the upper surface 54' of the sample 52' immediately surrounding the location from which that data point was derived. If the second microprocessor 10' finds a cluster or group of flaw data points derived from adjacent locations on the upper surface 54', it extracts the flaw data point having the largest digitized, modified amplitude value from the group. The second microprocessor 110' then replaces the group with that single, most significant data point and determines the size of the flaw based on a comparison of the digitized, modified amplitude value associated with that single, most significant data point with the calibration values.

Most preferably, the second microprocessor 110' will replace each such group of data points with a single, most significant data point to form an adjusted set of flaw data points before it classifies the flaw data points by size or location relative to the upper surface 54'. This is so that the second microprocessor 110' can detect any clusters or groups of flaw data points derived from adjacent locations on the upper surface 54' before the order of the data points in the raw data file (not shown) is deranged by the process of categorizing the flaw data points.

It is known that different types of flaws 72' can have different effects on the waveform characteristics, such as phase, of the echoes 64'. Thus, in some applications, it may be desirable to include the digital oscilloscope 95' or comparable means to monitor the digitized, modified amplitude signals for waveform phase inversion and to compare the digitized, modified amplitude signals obtained from the sample 52' with the calibration values. In particular, information concerning the physical characteristics of the flaws 72' can be derived from comparison of the digitized, modified amplitude signals with calibration values derived from tests conducted on reference samples (not shown) having compositions similar to those of the test sample 50' (FIG. 4), 52' and different types of artificially-created flaws (not shown). Examples of such artificially-created flaws (not shown) include blind, flat-bottom holes of fixed depth and diameter (not shown); and refractory particles of given size (not shown) artificially embedded into reference samples material (not shown), such as alumina particles in an aluminum or aluminum alloy target. Although such analysis provides additional information regarding the cleanliness of a material sample, those skilled in the art will recognize that such analysis is not critical to the present invention.

The second microprocessor 110' also determines a total number of data points "$C_{DP}$" in the region of the upper surface 54' scanned by the transducer 60' which yield information regarding the presence or absence of flaws; in other words, "$C_{DP}$" equals the sum of the flaw count $C_F$ (or of a series of flaw counts "$C_{F1}$," . . . "$C_{Fn}$" representing numbers of flaws classified according to flaw size, position relative to a region of interest (not shown) of the upper surface 54' or the like) and the number of no-flaw data points. Although $C_{DP}$ could be determined by adding counts of the flaw data points and the no-flaw data points, it is preferably determined by counting the total number of positions "$C_1$" along the region of interest (not shown) of the upper surface 54' at which the sample 52' is irradiated by the transducer 60' and subtracting the number of digitized signals "$C_N$" which the data acquisition circuitry was unable, due to noise or other causes, to identify as either flaw data points or no-flaw data points.

Having determined the flaw count $C_F$ (or multiple flaw counts "$C_{F1}$," . . . "$C_{Fn}$") and the total number of data points "$C_{DP}$," the second microprocessor 110' is programmed to calculate one or more cleanliness factors $F_{Cm}=(C_{Fm}/C_{DP})\times 10^6$ to characterize the material comprising the samples 50' (FIG. 4), 52'. The preparation of a suitable program for determining these one or more cleanliness factors in accordance with the invention as disclosed herein is within the ordinary skill in the art and requires no undue experimentation.

Another way in which to characterize the material comprising the samples 50' (FIG. 4), 52' is by determining the size distribution of flaws in the test sample 52'. More specifically, one may characterize the cleanliness of the sample 52' by defining amplitude bands or ranges; comparing the amplitudes of the digitized, modified amplitude signals with the amplitude bands to form subsets of the modified amplitude signals; counting these subsets of modified amplitude signals to determine a modified amplitude signal count for each amplitude band; and constructing a histogram (not shown) relating the modified signal counts to said plurality of amplitude bands. Since the amplitudes represented by the digitized modified amplitude signals are related to the sizes of flaws detected in the sample 52', the histogram (not shown) provides an indication of the flaw size distribution in the sample 52'.

Figure 6:
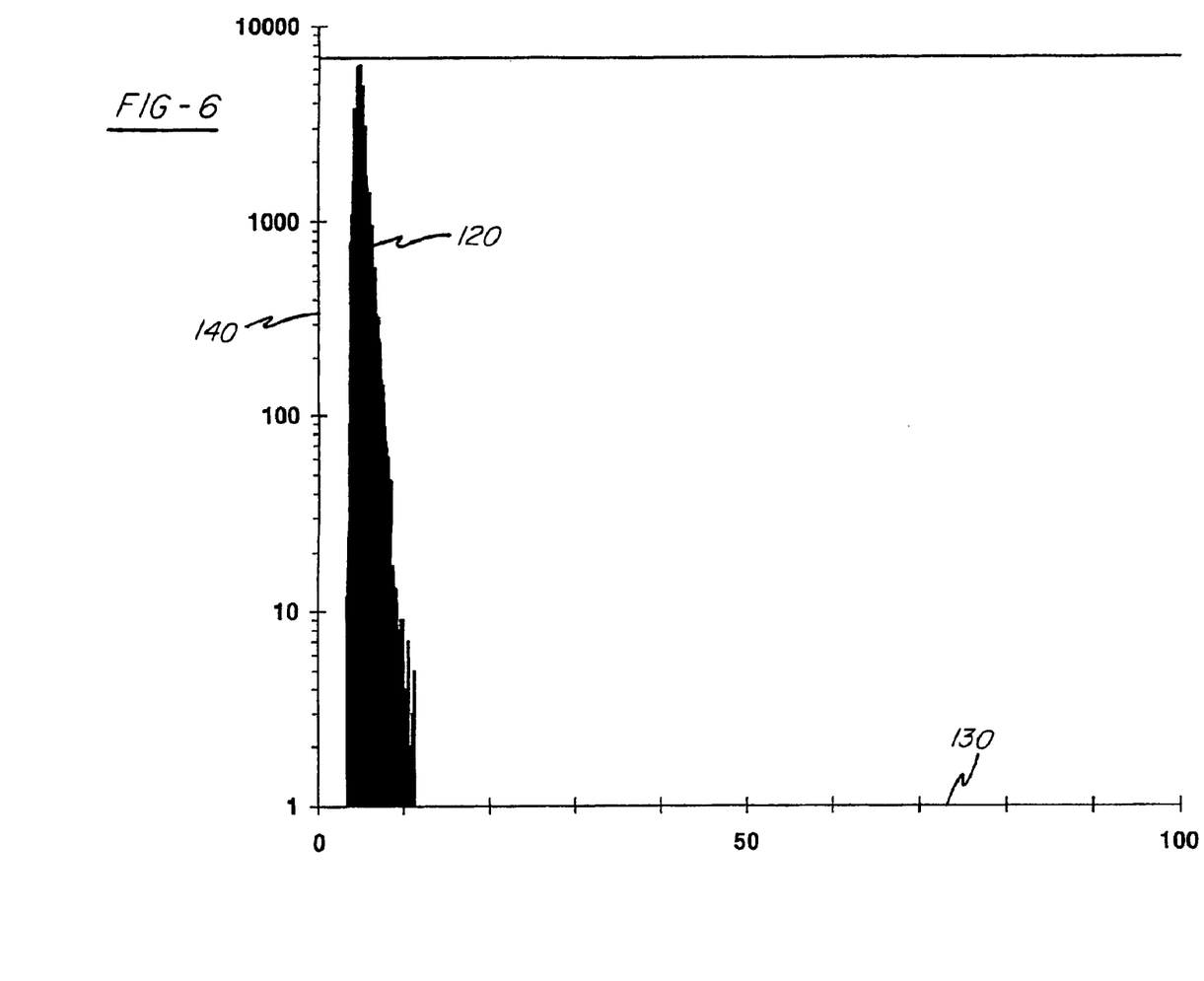
FIG. 6 is a histogram characterizing a relatively "clean" Al-0.2Si-0.5 wt % Cu material in accordance with an especially-preferred form of the invention.
Figure 7:
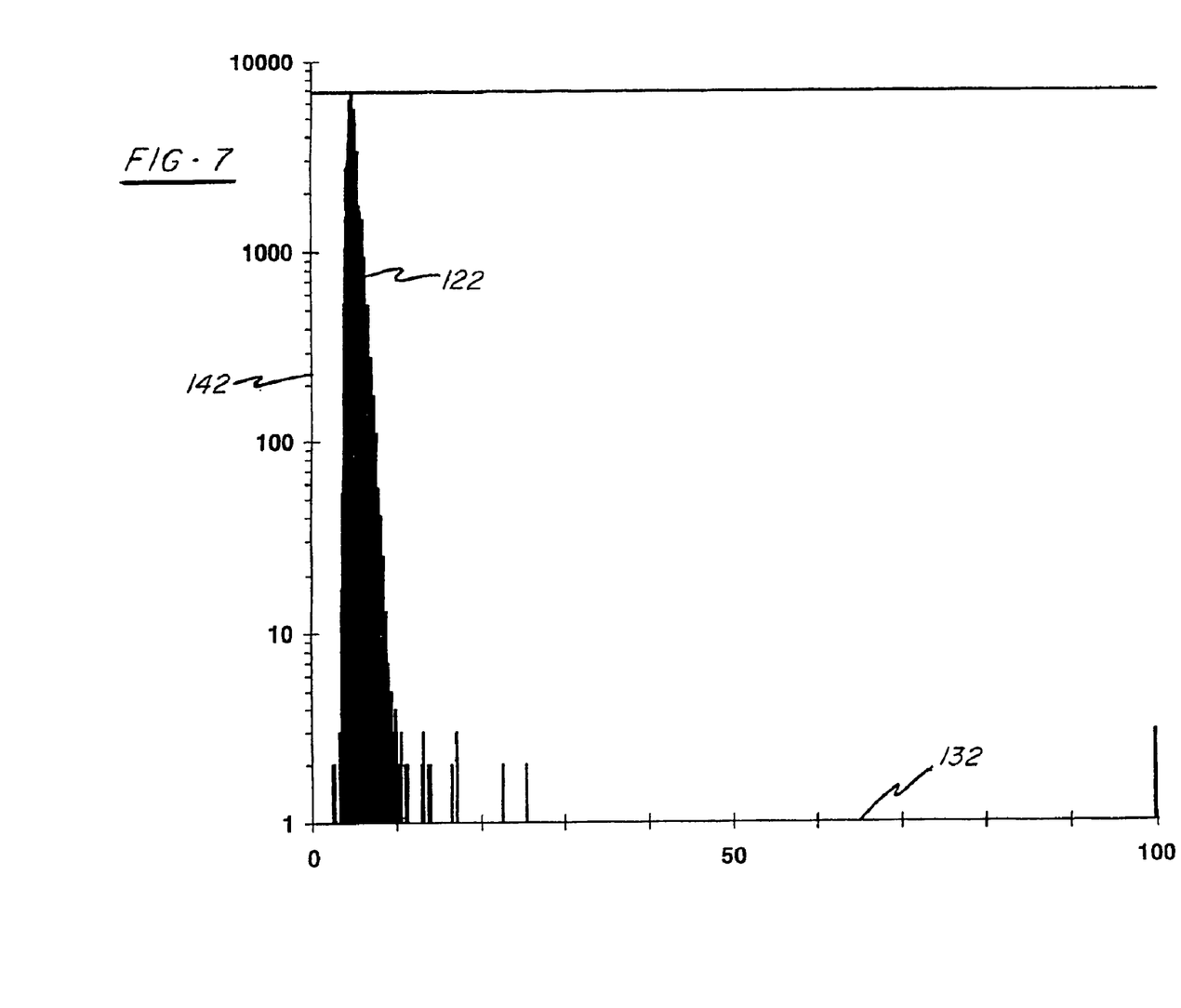
FIG. 7 is a histogram characterizing a less "clean" Al-0.2Si-0.5 wt % Cu material in accordance with the especially-preferred form of the invention.

Turning now to FIGS. 6 and 7, there may be seen histograms 120 (FIG. 6) and 122 (FIG. 7) characterizing two Al/0.2 wt % Si/0.5 wt % Cu alloy sputter target materials (not shown) having orthorhombic textures and grain sizes in the range of 0.08 mm to 0.12 mm. Each material was deformed into a disc-shaped sample having a surface area of approximately 78.4 in$^2$ (506 cm$^2$) and irradiated at approximately $6.4\times10^4$ positions. The material of FIG. 6 was "cleaner" ($F_C\approx 47$) than that of FIG. 7 ($F_C\approx 125$). The thickness zone of flaw monitoring was located within a gate of 4.5 microsecond duration with a gate delay of 1.5 microseconds.

The abscissae 130 (FIG. 6), 132 (FIG. 7) of the histograms of FIGS. 6 and 7 represent amplitude normalized as a percentage of the echo amplitude induced in a reference sample (not shown) having a 0.8 mm blind, flat-bottom hole. The ordinates 140 (FIG. 6), 142 (FIG. 7) in FIGS. 6 and 7 represent the modified signal counts for each amplitude, expressed on a logarithmic scale. The echo amplitude thresholds for the flaw counts were set to 15.9% since, as established experimentally, the texture-related echo amplitude did not exceed 15% for all aluminum alloys tested. The preparation of a suitable program for plotting histograms such as the histograms 120 (FIG. 6), 122 (FIG. 7) shown in FIGS. 6 and 7 in accordance with the invention as disclosed herein is within the ordinary skill in the art and requires no undue experimentation.

From the foregoing, it will be apparent that one object of the present invention is to provide a non-destructive method for characterizing the cleanliness of a sputter target material which is capable of distinguishing the sizes and locations of flaws detected in the material. It will be apparent that another object of the present invention is to provide a method capable of distinguishing single, relatively large flaws from a plurality of smaller, closely spaced flaws. It will be apparent that another advantage of the invention is to provide a relatively efficient method capable of performing simultaneous data acquisition and data processing on different material samples in a queue.

While the method and form of apparatus herein described constitutes a preferred embodiment of this invention, it is to be understood that the invention is not limited to this precise method and form of apparatus, and that changes may be made therein without departing from the scope of the invention which is defined in the appended claims.

What is claimed is:

1. A non-destructive method for characterizing a test sample of a sputter target material defining a surface, said method using one or more calibration values and comprising the steps of:
   a) sequentially irradiating the test sample with sonic energy at a plurality of positions on the surface;
   b) detecting echoes induced by the sonic energy;
   c) discriminating texture-related backscattering noise from the echoes to obtain modified amplitude signals;
   d) comparing the modified amplitude signals with the one or more calibration values to detect
      i) flaw data points at certain positions of the plurality of positions where comparison of the modified amplitude signals with the one or more calibration values indicates at least one flaw, and
      ii) no-flaw data points at other positions of the plurality of positions where comparison of the modified amplitude signals with the at least one calibration value indicates no flaw;
   e) binding groups of the flaw data points corresponding to single large flaws so as to generate an adjusted set of flaw data points in which each group of the groups of flaw data points is replaced with a single, most significant data point;

f) counting members of the adjusted set of flaw data points to determine at least one flaw count $C_F$;

g) determining a total number of data points $C_{DP}$; and h) calculating a cleanliness factor $F_c=(C_F/C_{DP})\times10^6$.

2. The method as recited in claim 1 wherein the surface defines a sputter track region; each flaw data point is associated with one of the plurality of positions; and substantially all of the members of the adjusted set of flaw data points are associated with positions of the plurality of positions located proximate the sputter track region.

3. The method as recited in claim 1 including the additional step of classifying the members of the adjusted set of flaw data points according to ranges of size to form a plurality of subsets of size-classified flaw data points, where "n" represents the number of sets in the plurality of subsets of size-classified flaw data points; said step f) includes counting members of the plurality of subsets of size classified flaw data points to determine flaw counts $C_{F1}, \ldots C_{Fn}$; and said step h) includes calculating a plurality of cleanliness factors $F_{Cj}=(C_{Fj}/C_{DP})\times10^6$.

4. The method as recited in claim 1 including the additional step of classifying the members of the adjusted set of flaw data points into a first subset of flaw data points representing flaws of flaw size equal or smaller than 0.5 mm, a second subset of flaw data points representing flaws of flaw size in the range of 0.5 mm to 0.8 mm, and a third subset of flaw data points representing flaws of flaw size equal or larger than 0.8 mm; said step f) includes counting members of the first subset of flaw data points to determine a first flaw count $C_{F1}$; said step f) further includes counting members of the second subset of flaw data points to determine a second flaw count $C_{F2}$; said step f) further includes counting members of the third subset of flaw data points to determine a third flaw count $C_{F3}$; said step h) includes calculating a first cleanliness factor $F_{C1}=(C_{F1}/C_{DP})\times10^6$; said step h) further includes calculating a second cleanliness factor $F_{C2}=(C_{F2}/C_{DP})\times10^6$; and said step h) further includes calculating a third cleanliness factor $F_{C3}=(C_{F3}/C_{DP})\times10^6$.

5. The method as recited in claim 1 including the additional step of determining the calibration values by irradiating a reference sample comprising blind, flat-bottomed, holes of fixed depth and diameter; detecting at least one echo induced by the sonic energy; and discriminating texture-related backscattering noise from the at least one echo to obtain the one or more calibration values.

6. The method as recited in claim 1 including the additional step of determining the calibration values by irradiating a reference sample comprising alumina particles of given size artificially embedded; detecting at least one echo induced by the sonic energy; and discriminating texture-related backscattering noise from the at least one echo to obtain the one or more calibration values.

7. The method as recited in claim 1 including the additional step of deforming a cylindrical sample to disc shape to form said test sample prior to said step a).

8. A non-destructive method for characterizing a test sample of a sputter target material defining a surface, said method using one or more calibration values and comprising the steps of:

a) sequentially irradiating the test sample with sonic energy at a plurality of positions on the surface;

b) detecting echoes induced by the sonic energy;

c) discriminating texture-related backscattermg noise from the echoes to obtain modified amplitude signals;

d) comparing the modified amplitude signals with the one or more calibration values to detect i) flaw data points at certain positions of said plurality of positions where comparison of the modified amplitude signals with the one or more calibration values indicates at least one flaw, and ii) no-flaw data points at other positions of said plurality of positions where comparison of the modified amplitude signals with the at least one calibration value indicates no flaw;

e) binding groups of said flaw data points corresponding to single large flaws so as to generate an adjusted set of flaw data points in which each group of the groups of flaw data points is replaced with a single, most significant data point;

f) defining a plurality of amplitude bands;

g) comparing the amplitudes represented by members of the adjusted set of flaw data points with the amplitude bands to form a plurality of subsets of the adjusted set of flaw data points, where "n" is the number of the subsets of the adjusted set of flaw data points;

h) counting members of the subsets of the adjusted set of flaw data points to determine a plurality of flaw counts $C_{F1}, \ldots C_{Fn}$; and i) constructing a histogram relating said flaw counts $C_{F1}, \ldots C_{Fn}$ to said amplitude bands.

9. The method as recited in claim 8 wherein the surface defines a sputter track region; each flaw data point is associated with one of the plurality of positions; and substantially all of the members of the adjusted set of flaw data points are associated with positions of the plurality of positions located proximate the sputter track region.

10. The method as recited in claim 8 including the additional step of determining the calibration values by irradiating a reference sample comprising blind, flat-bottomed, holes of fixed depth and diameter; detecting at least one echo induced by the sonic energy; and discriminating texture-related backscattering noise from the at least one echo to obtain the one or more calibration values.

11. The method as recited in claim 8 including the additional step of determining the calibration values by irradiating a reference sample comprising alumina particles of given size artificially embedded; detecting at least one echo induced by the sonic energy; and discriminating texture-related backscattering noise from the at least one echo to obtain the one or more calibration values.

12. The method as recited in claim 8 including the additional step of deforming a cylindrical sample to disc shape to form said test sample prior to said step a).

13. Apparatus for non-destructive characterization of a test sample of a sputter target material defining a surface, said apparatus comprising:

a) an ultrasonic transducer for irradiating the test sample with sonic energy and detecting echoes induced by the sonic energy to generate RF electric amplitude signals;

b) an X-Y scanner mounting said ultrasonic transducer for controlled movement of said ultrasonic transducer relative to said surface;

c) a pre-amplifier for receiving and amplifying said RF electric amplitude signals;

d) a linear amplifier with a set of calibrated attenuators for generating modified amplitude signals related to said RE electric amplitude signals;

e) an analog-to-digital converter for receiving said modified amplitude signals and generating digital signals related to said modified amplitude signals; and f) a microprocessor controller programmed to regulate the controlled movement of said ultrasonic transducer relative to the surface, to receive said digital signals, to compare the modified amplitude signals with the one or more calibration values to detect
  i) flaw data points at certain positions of said plurality of positions where comparison of the modified amplitude signals with the one or more calibration values indicates at least one flaw and
  ii) no-flaw data points at other positions of said plurality of positions where comparison of the modified amplitude signals with the at least one calibration value indicates no flaw, to bind groups of said flaw data points corresponding to single large flaws so as to generate an adjusted set of flaw data points in which each group of the groups of flaw data points is replaced with a single, most significant data point, to count members of the adjusted set of flaw data points to determine at least one flaw count $C_F$, to determine a total number of data points $C_{DP}$, and to calculate a cleanliness factor $F_c=(C_F/C_{DP})\times 10^6$.

14. The apparatus as recited in claim 13 wherein said microprocessor controller includes a first microprocessor and a second microprocessor.

15. The apparatus as recited in claim 13 wherein said microprocessor controller includes a first microprocessor and a second microprocessor;

said first microprocessor being programmed to regulate the controlled movement of said ultrasonic transducer relative to the surface, to receive said digital signals, and to transfer said digital signals to said second microprocessor; and said second microprocessor being programmed to compare the modified amplitude signals with the one or more calibration values to detect
  i) flaw data points at certain positions of said plurality of positions where comparison of the modified amplitude signals with the one or more calibration values indicates at least one flaw and
  ii) no-flaw data points at other positions of said plurality of positions where comparison of the modified amplitude signals with the at least one calibration value indicates no flaw, to bind groups of said flaw data points corresponding to single large flaws so as to generate an adjusted set of flaw data points in which each group of the groups of flaw data points is replaced with a single, most significant data point, to count members of the adjusted set of flaw data points to determine at least one flaw count $C_F$, to determine a total number of data points $C_{DP}$, and to calculate a cleanliness factor $F_c=(C_F/C_{DP})\times 10^6$.

* * * * *

UNITED STATES PATENT AND TRADEMARK OFFICE
CERTIFICATE OF CORRECTION

PATENT NO. : 6,895,342 B2
DATED : May 17, 2005
INVENTOR(S) : Alexander Leybovich It is certified that error appears in the above-identified patent and that said Letters Patent is hereby corrected as shown below:

Column 14,
Line 62, delete "RE" and substitute -- RF --.

Signed and Sealed this

Nineteenth Day of July, 2005

JON W. DUDAS
*Director of the United States Patent and Trademark Office*